United States Patent [19]
McMillen et al.

[11] Patent Number: 5,435,321
[45] Date of Patent: Jul. 25, 1995

[54] JOINT DISPLACEMENT MEASUREMENT APPARATUS

[75] Inventors: Robert J. McMillen, Encinitas; Michael A. Faltys, San Diego; Carl A. Moran, Jr., Encinitas, all of Calif.

[73] Assignee: E.V.C., Encinitas, Calif.

[21] Appl. No.: 164,565

[22] Filed: Dec. 10, 1993

[51] Int. Cl.⁶ .................................... A61B 5/00
[52] U.S. Cl. ......................... 128/782; 128/774; 33/511; 33/515
[58] Field of Search ............ 128/774, 781, 782; 33/511, 512, 519.2, 515

[56] References Cited

U.S. PATENT DOCUMENTS

| | | | |
|---|---|---|---|
| T100,602 | 5/1981 | Roley et al. | 128/682 |
| 3,270,558 | 9/1966 | Barret et al. | 128/782 X |
| 4,030,213 | 7/1977 | Gregory | 128/781 |
| 4,549,555 | 10/1985 | Fraser et al. | 128/782 |
| 4,823,807 | 4/1989 | Russell et al. | 128/782 X |
| 4,909,262 | 3/1990 | Halpern et al. | 128/774 |
| 5,088,504 | 2/1992 | Benesh et al. | 33/515 X |
| 5,121,753 | 6/1992 | Paez | 33/515 X |
| 5,263,492 | 11/1993 | Voyce | 128/782 |

Primary Examiner—Sam Rimell
Attorney, Agent, or Firm—Brown, Martin, Haller & McClain

[57] ABSTRACT

The measurement device includes a frame with a support and mounting member, a longitudinal bar, a lateral bar pivotally and slidably attached to the longitudinal bar with a pair of stirrups or heel cups attached symmetrically on either side of the longitudinal bar at a known distance from the longitudinal bar. A plurality of potentiometers or other resistive measurement devices are attached to the two bars to provide analog measurements of lengthwise and angular displacement. A microprocessor controller calculates actual leg length and offset by combining the measurements obtained from the first two resistive elements using a simple trigonometric function. An output means in the form of an LED and/or LCD display provides a visual display of the calculated actual and offset values.

23 Claims, 4 Drawing Sheets

JOINT DISPLACEMENT MEASUREMENT APPARATUS

BACKGROUND OF THE INVENTION

Activator method is a widely practiced chiropractic technique which involves the application of a measured thrust action to pressure points on the body to make adjustments, much like the ancient oriental technique of accupressure. The thrust is provided by a spring-loaded mallet activator instrument with a rubber tip that is positioned at the appropriate pressure point to relieve the improper muscle tension. Determination of where the thrust action is to be applied is made by a number of measurements, an important one of which consists of observing the relative lengths of the patient's legs while the patient is lying on a table. The amount of offset and which leg is longer will give the chiropractor an indication of the degree and source of the patient's misalignment. Typically, however, this "measurement" is inexact because there are no tools available for making a quantitative measurement, and the determination is solely based on the practitioner's visual examination. While the inexact visual estimation method may not significantly impact the quality of treatment, it does limit the practitioner's ability to maintain records of the patient progress or of recurring conditions. Further, where records are required for submission of insurance claims, the ability to provide quantitative measurements would be advantageous.

Leg length comparison for determination of where pressure is to be applied in activator or other chiropractic techniques is effective because the variation in leg length is due to joint displacement caused by muscle tension. Therefore, any variations in muscle tension which induce joint displacement would also be quantifiable using a technique that would be effective in measuring relative leg lengths.

A number of other physiological studies can benefit by using measurements similar to those utilized by chiropractors who practice the activator technique. Among these techniques are applied kinesiology, sacrooccipital technique, Brodie major/minor system (measures arm length), acupuncture point testing, nutritional testing, emotional engram testing, and allergy testing, among others.

SUMMARY OF THE INVENTION

It is an advantage of the present invention to provide a method and apparatus for quantitative measurement of joint displacement which may be used for chiropractic treatment and other diagnostic testing.

It is another advantage of the present invention to provide a method and apparatus for detection of neuromuscular response by measuring joint displacement.

Still another advantage of the present invention is to provide an apparatus and method for maintaining numerical records for establishing patient histories.

In an exemplary embodiment, the apparatus of the present invention for measurement of leg lengths comprises a frame with a support and mounting member, a longitudinal bar, a lateral bar pivotally and slidably attached to the longitudinal bar with a pair of stirrups, ankle braces or heel cups attached symmetrically on either side of the longitudinal bar at a known distance from the longitudinal bar. A plurality of resistive or optical measurement devices are attached to the two bars to measure lengthwise and angular displacement.

The support and mounting member provide attachment of the apparatus to the treatment table and preferably are pivotally mounted to allow the entire apparatus to swing away from or into the table. The support and mounting member also can have a telescoping component to allow the apparatus length to be adjusted for different size patients, e.g., adults and children.

The longitudinal bar has a lengthwise slot into which the transverse bar is slidably retained. The slide portion of the transverse bar cooperates with a resistive strip or a belt/potentiometer combination so that the position of the slide along the length of the longitudinal bar can be electrically measured. The pivoting action of the transverse bar with respect to the longitudinal bar is measured by a second resistive element, which measures the angle from perpendicular to the longitudinal bar. A third resistive element or potentiometer is used to measure the angle between the longitudinal bar and the support member which is representative of the knee bend angle. The desired knee bend angles for the activator technique measurement of relative leg length can be between 0 degrees (horizontal) and 120 degrees. The third potentiometer provides an indication of the angle at which the knees are bent.

A microprocessor controller calculates actual leg length and offset by combining the measurements obtained from the first two resistive elements using a simple trigonometric function. Output means in the form of LED and LCD displays provide a visual display of the calculated actual and offset values.

BRIEF DESCRIPTION OF THE DRAWINGS

Understanding of the present invention will be facilitated by consideration of the following detailed description of a preferred embodiment of the present invention, taken in conjunction with the accompanying drawings, in which like reference numerals refer to like parts and in which.

DETAILED DESCRIPTION OF A PREFERRED EMBODIMENT

Figure 1:
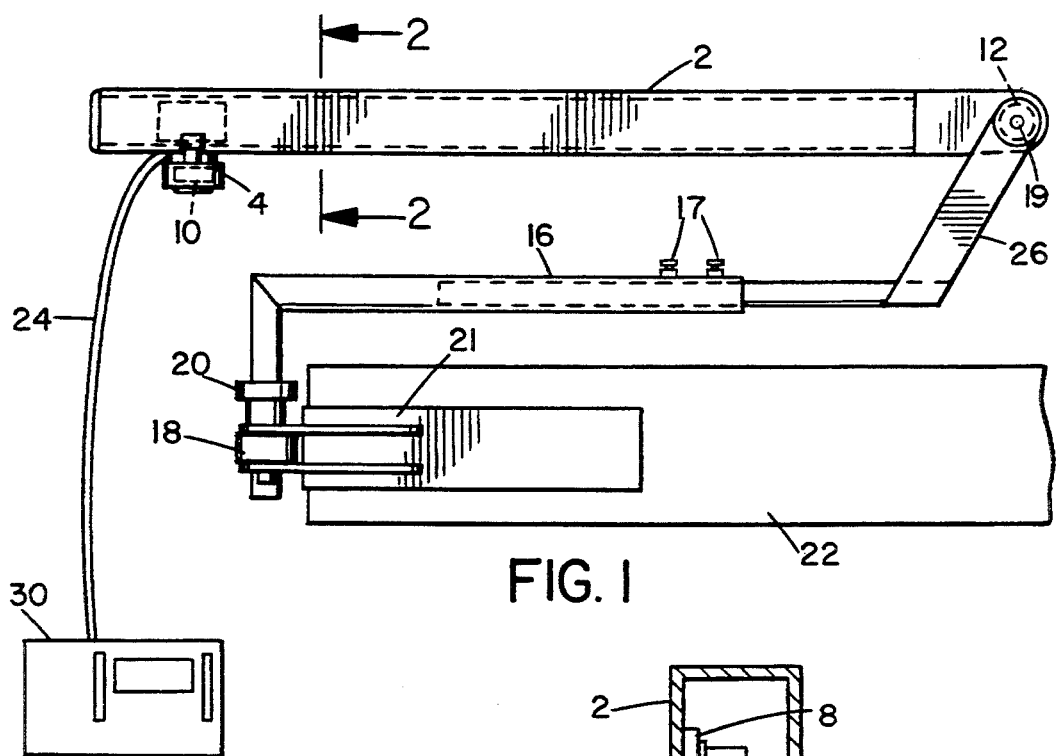
FIG. 1 is a side elevation of the apparatus according to the present invention.
Figure 3:
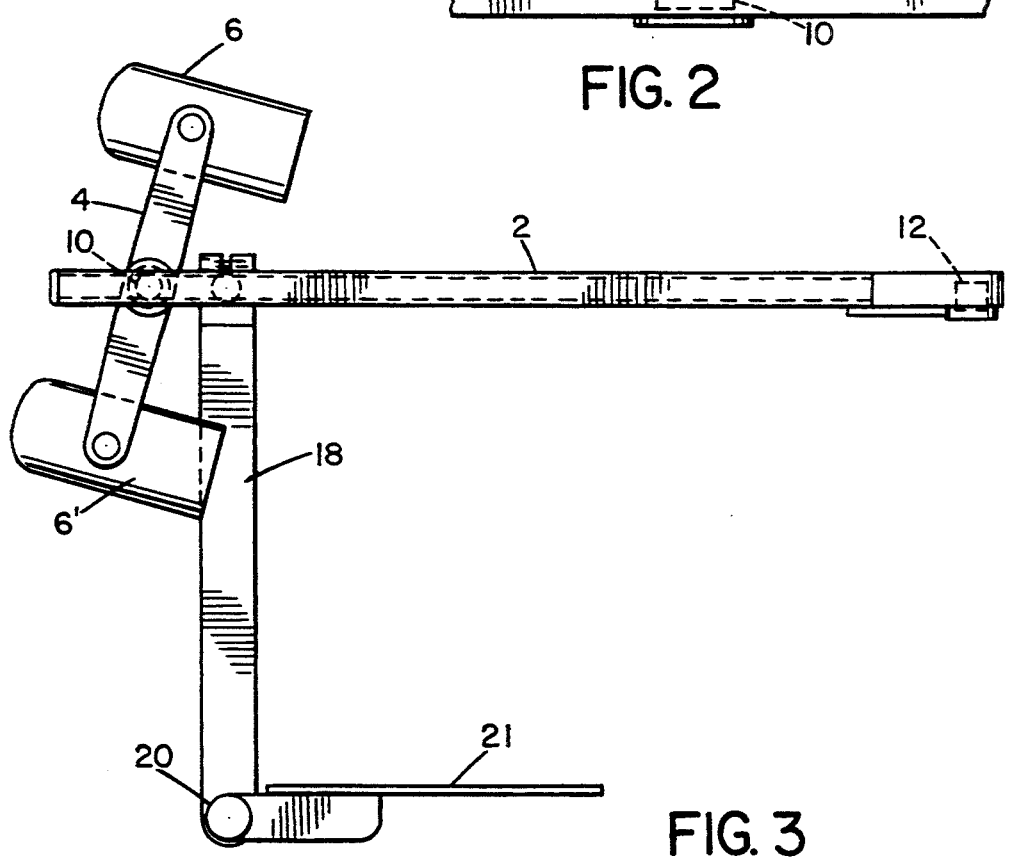
FIG. 3 is a top view of the apparatus.
Figure 4:
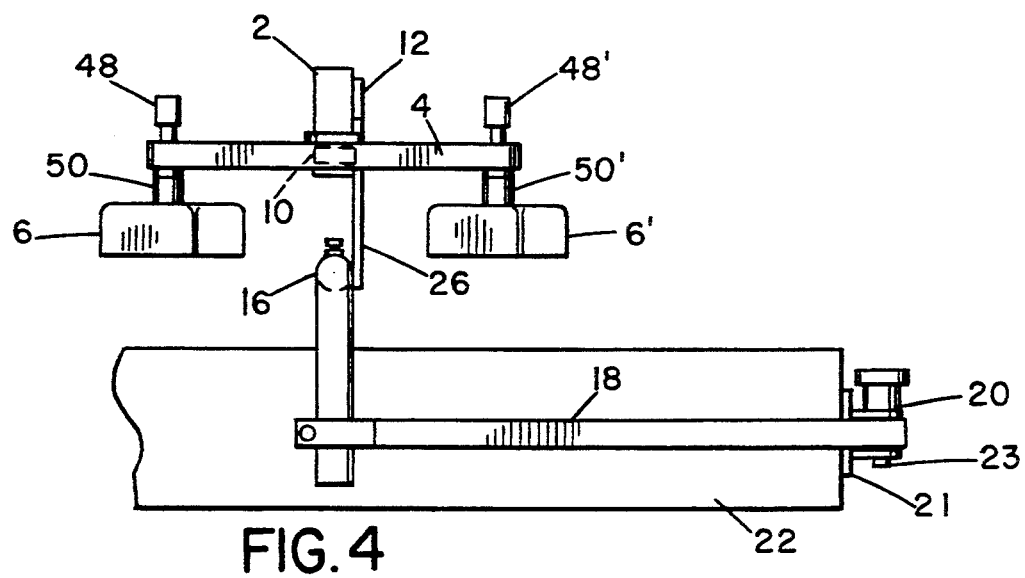
FIG. 4 is a back elevation of the apparatus.

As illustrated in FIGS. 1, 3 and 4, the activator measurement apparatus comprises a longitudinal bar 2, a transverse bar 4, a pair of stirrups 6 and 6', means for attaching the stirrups to transverse bar 4, and resistive elements 8, 10 and 12 for measuring lengths and angles of the bars 2 and 4. A support frame includes a longitudinal extension 16, a lateral extension 18, and a vertical mounting attachment 20 which attaches to a treatment table 22. The controller 30 is connected to resistive elements 8, 10 and 12 by cable 24. Controller 30, shown in more detail in FIG. 6, includes LCD display 32, LED display 34, analog-to-digital converter 35, microcontroller 36, program memory means 38, input means 40, and audible signal means 42.

Vertical mounting attachment 20 may be fixed to the corner at the foot of treatment table 22 by attachment plate 21 and includes a pivoting connection 23 so that it can be pivoted out away from the table to allow the patient to get on the table 22. Lateral extension 18 extends from the corner of the table 22 generally along its edge to its center so that the measurement apparatus bisects the table and will be centered between the patients legs. Longitudinal extension 16 extends toward the head of the table and is of adjustable length, to permit adaptation of the device for different size patients. For example, as illustrated in FIG. 1, the extension 16 may be a telescoping tube with locking means 17 to maintain the extension at the desired length once the length has been determined. An extension 26 attaches to the end of extension 16 and angles upward for pivotable attachment to longitudinal bar 2. Extension 16 is used to allow measurement of a wide range of leg lengths and may provide the ability to measure actual leg length. It may also be desirable to adjust the length of the extension 16 so that the pivot point 19 of longitudinal bar 2 and extension 26 corresponds to the patient's knee joint.

Figure 7:
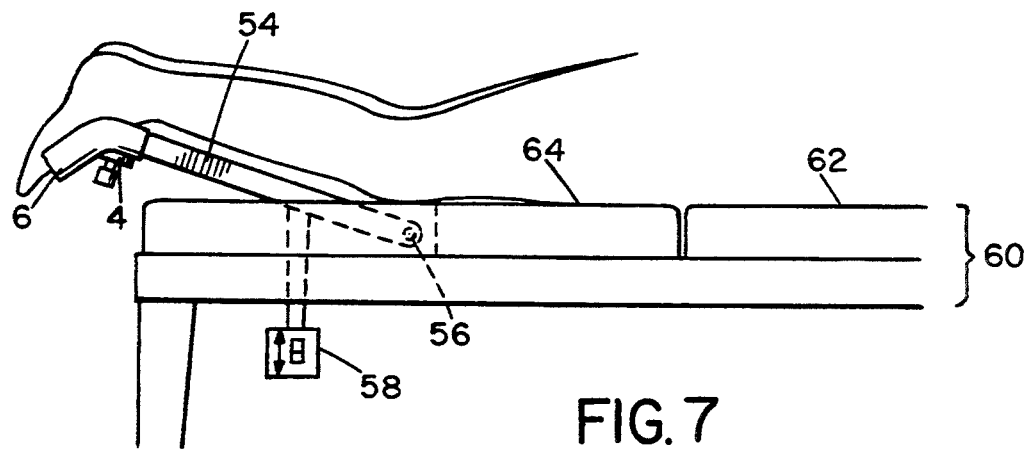
FIG. 7 is a side elevation of an alternate embodiment of the invention.
Figure 8:
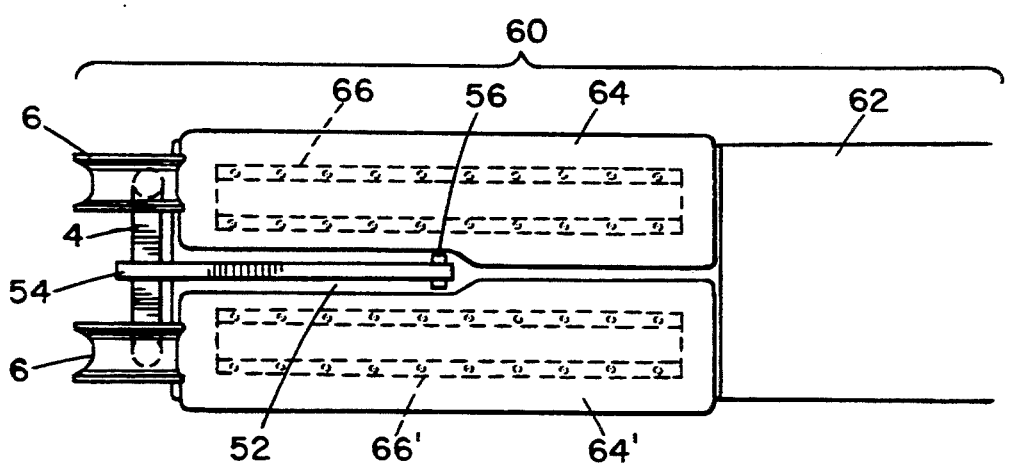
FIG. 8 is a top view of a modified treatment table for improved accuracy of measurement.

An alternative mounting means is illustrated in FIGS. 7 and 8. In this embodiment, the treatment table 60 can be constructed so that it is split in the middle, leaving a slot 52 into which the longitudinal bar 54 can be recessed. Longitudinal bar 54 pivots in and out of slot 52 at pivot point 56, with its height above the table 60 being controlled by height adjustment 58, which can be manually or electrically driven. The transverse bar 4 and ankle supports 6 extend off of the end of the table.

Figure 2:
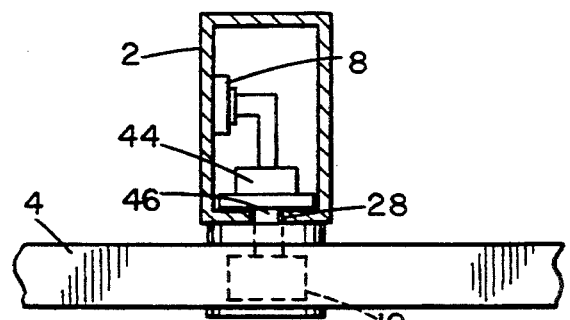
FIG. 2 is a cross-sectional view taken along line 2—2 of FIG. 1.

As illustrated in FIG. 2, longitudinal bar 2 has a lengthwise slot 28 within which slide 44 slides. A linear resistive element 8 is disposed within longitudinal bar 2 in contact with slide 44 to generate an electrical signal representative of the position of slide 44 within longitudinal bar 2. This electrical signal is provided to controller 30 to provide a measurement of leg length from the pivot point between extension 16 and longitudinal bar 2. As an alternative to linear resistive element 8, an optical detector and encoder may be used. Similarly, all other measurement devices for detection of position or angle and generation of an electrical signal representative thereof which are described in the preferred embodiment as resistive elements may alternatively be optical detectors.

Extension 46 attaches generally perpendicularly (along the z-axis) to slide 44, extending downward where it pivotally attaches to transverse bar 4. Resistive element 10, a potentiometer, is attached to extension 46, providing output resistance values corresponding to angular deviation (within the x,y-plane) of transverse bar 4 from perpendicular to longitudinal bar 2.

The frame components, bars and various extensions are made from metal tubing, either round or square, or channels. The metal used may be aluminum, stainless steel, bronze, or other metal which possesses the requisite strength. It may also be possible to make these components from a durable plastic or polymer which can be molded or machined to the desired configuration.

As illustrated in FIG. 3, stirrups 6 and 6' attach to the ends of transverse bar 4 located symmetrically on either side of longitudinal bar 2 by way of snaps or bolts (shown as male fasteners 48 and 48') in transverse bar 4 which are designed to be easily mated with or released from corresponding sockets 50 and 50' in stirrups 6 and 6'. The distance between the longitudinal bar 2 and bolts 48 and 48' may be adjustable for the comfort of the patient, by providing a number of different fastening holes 50 and 50' in the transverse bar, but must be fixed for any given series of measurements on the patient, since the distance is one of the parameters used to calculate leg length offset. If variability of this distance is provided, the selected distance must be entered into the controller 30 to assure that the correct parameters are used in the calculations.

The stirrups 6 and 6' may be formed from molded polyethylene or a similar polymer or plastic, shaped as a cup to conform to the patient's heel and ankle. The stirrups may be put on the patient's feet before he or she gets on the table, then snapped into the transverse bar. The patient's feet are held in the stirrups 6 and 6' with straps 52, which may be nylon webbing or neoprene attached with a hook and pile fastener such as Velcro TM, or the straps may be made entirely from Velcro TM. Other fasteners, such as snaps, buckles or hooks and eyes may also be used. The stirrups may also be lined with padding, such as neoprene, for additional comfort. As an alternative to the stirrups, straps directly attached to the transverse bar may be fastened around the patient's ankles, or spring clips may be used to grip the sides of the patient's shoes. Although the device is shown in use with the patient in the prone position in FIG. 5, it is also possible to position the device for measurement with the patient in the supine position. For the latter situation, the device may be positioned so that it extends off of the end of the table.

A modification of the treatment table facilitates measurement of leg offset by removing any friction between the table top and the patient's upper legs that could impede accurate measurement of relative leg length. As illustrated in FIG. 8, treatment table 60 consists of three segments. The top segment 62 is fixed and will bear the weight of the patient's torso. The lower two segments 64 and 64' are split and mounted on roller bearing glide rails 66 and 66' to allow them to move freely along the length of the rails. The measurement apparatus is recessed between segments 64 and 64' and operates the same as the embodiment of FIG. 7. The virtually frictionless glide of the segments 64 and 64' on the rails 66 and 66' removes any resistance that might cause an erroneous measurement of offset.

Figure 5:
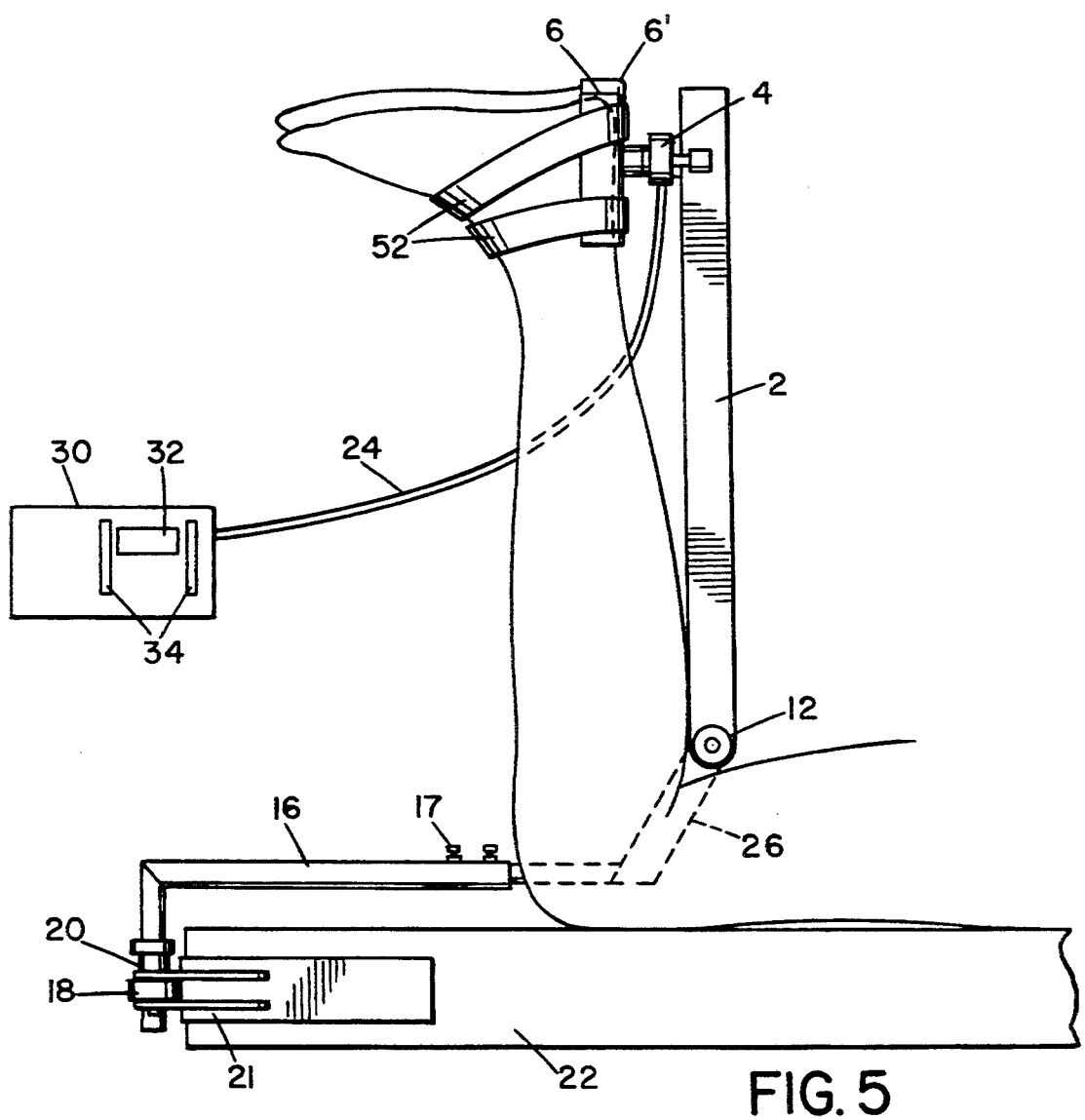
FIG. 5 is a side elevation of the apparatus according to the present invention in use on a patient.

Since different chiropractors who use the activator technique use different methods for evaluating relative leg length, a third resistive element 12 is provided to indicate the patient's knee-bend angle. Some practitioners prefer to measure the relative leg length with the knees straight, i.e., knee angle of 0 degrees. Others measure relative leg length with the knees bent at some non-zero angle, which can be up to 120 degrees. As shown in FIG. 5, the measurement is being taken at 90 degrees. (The latter may be preferred by practitioners because the leg length difference will show more clearly.) Using the example illustrated, to assure that the knee-bend is actually 90 degrees, rather than trying to visually estimate, resistive element 12 measures the angle, and the controller 30 is set up to provide an indication, usually by an audible signal and/or flashing LEDs, that the 90 degree bend has been achieved. This permits a more repeatable and precise measurement, and can be used at the practitioner's angle of preference. The measurement provided by the third resistive element, a potentiometer, is not otherwise used in calculation of the leg length offset.

Figure 6:
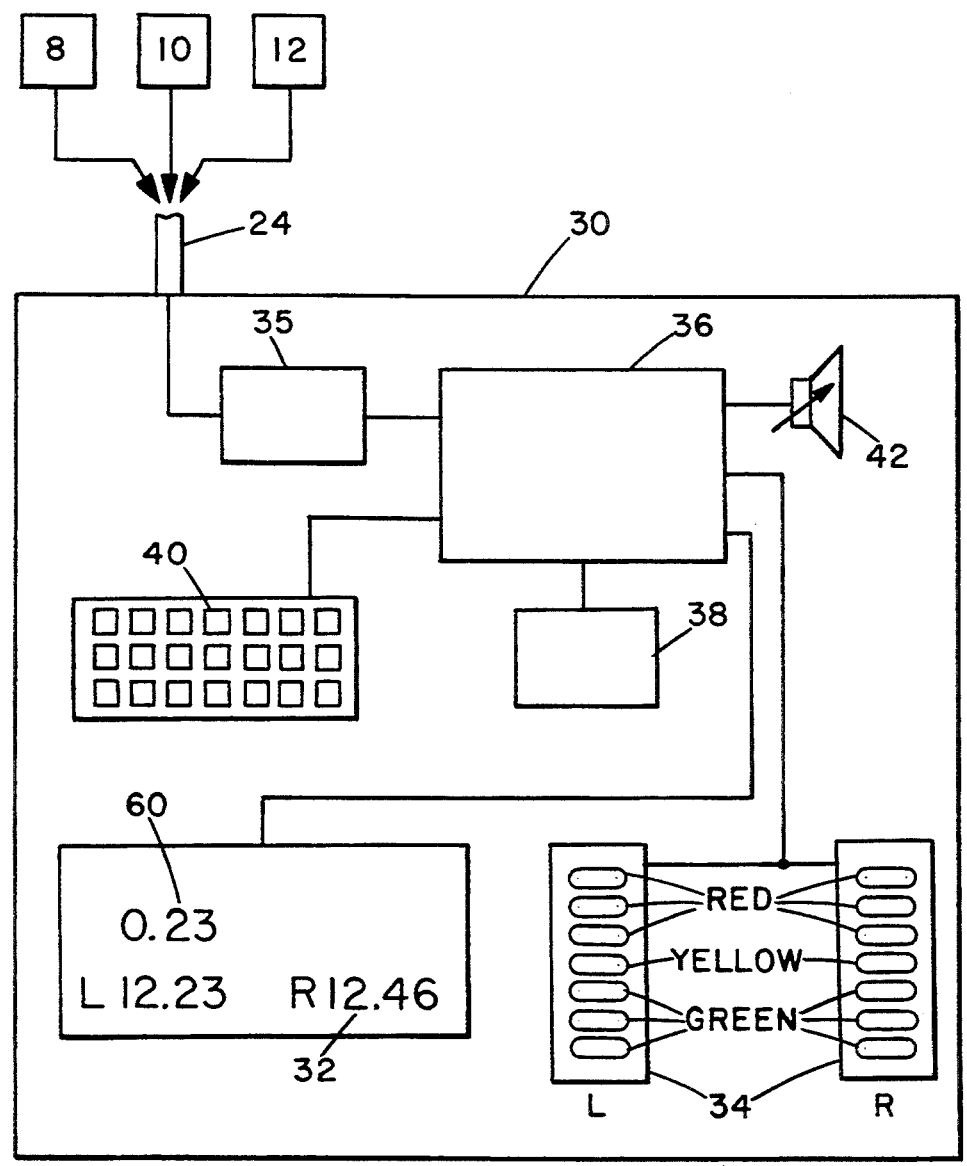
FIG. 6 is a block diagram of the controller.

The controller 30, shown in FIG. 6, receives the electrical signals provided by the various resistive elements through cable 24 and an analog-to-digital converter 35 converts the raw analog values into digital signals representative of length in inches (or in centimeters, if desired) and angle in degrees or radians. (The analog-to-digital converter 35 may be an integral part of the microcontroller.) This information is used by the microcontroller 36 to calculate the actual and offset leg lengths. The offset is calculated according to the relationship offset=$d\sin\theta$, where $\theta$ is the angle measured by resistive element 10 and d is the distance between extension 46 and bolt 48 or 48', i.e., one-half the distance between the patient's feet, so that the leg length is L±$d\sin\theta$. Attached as Appendix A is the assembly language program listing for the software for performing the calculations and providing output indications of the measurement results. This program, which includes a menu for input options, is stored in program memory 38, which may be an integral part of the microcontroller.

After calculation, the leg length and offset values are displayed on LCD display 32, an example of which is provided in FIG. 6. The offset value 60, of ΔL, is displayed above the leg which is shorter, which, in the illustrated case, is the left leg. The leg lengths shown are the distance from the patient's knee if the pivot point is aligned with the knee. It may also be used to modify the program output to show length from the patient's hip by entering into the processor a measurement of the patient's leg length to the device's pivot point.

During the adjustments that occur after the initial measurement is taken, the chiropractor will want to recheck the leg length offset. To make this process even easier to perform without requiring frequent comparison of earlier measurements, an LED display 34 is also provided to provide a qualitative display of changes in offset, in the form of one or more bar graphs. This display will also be easier to see at a distance, since the chiropractor may not be close enough to read the LCD display 32.

In the experimental prototype, the LED display consists of two separate rows of LEDs, one for each leg, each of which may be of different colors, for example, multiple LEDs each of red, yellow and green. When the red LEDs are lit for the right leg, for example, this means that the right leg is longer. The more red LEDs lit on the right side, the greater the offset in leg length. Since this means that the left leg will be shorter, the green LEDs in the row of LEDs for the left leg will be lit. When the legs are even, the yellow LEDs in both rows will be lit. In the figure, seven LEDs are shown: three red, one yellow and three green. If, for example, the offset is relatively large, all of the green LEDs will be lit along on the left side with all of the red LEDs lit on the right side. With each successive adjustment, the number of LEDs illuminated should decrease, until only the yellow LEDs are lit. This indicates that a normal or acceptable offset has been achieved. The LED scale factor can be set using the set-up menu to make it more or less sensitive. Thus, the amount of offset that will result in a peak reading, causing all of the red LEDs to be illuminated, can be adjusted, for example, within a range of 0.75 inch, for maximum sensitivity, to 2.0 inches, for minimum sensitivity but maximum range. The brightness of the LEDs can also be adjusted using the set-up menu to allow the display to be seen from a distance, or to compensate for ambient light. It may also be desirable to include a photodiode, phototransistor, or photocell within the controller to detect ambient light and automatically adjust the LED brightness. It should be noted that the above is merely an example of how the LEDs might be set up. The configuration of the visual bar graph display is not limited to this arrangement, nor is it limited to LEDs. LCD displays, gas discharge displays, video monitors, and any other type of numeric or alphanumeric display may be used to produce a bar graph display.

To further facilitate frequent checking during adjustment, an audible signal means 42 may be provided to allow the chiropractor to listen for changes in volume, pitch, tone and/or repetition rate, i.e., an audio bar graph, to indicate that improvements are being made and the offset has been decreased.

The controller 30 constantly scans for signals provided by the resistive elements 8, 10 and 12. As this information is received, it is converted by the analog-to-digital (A/D) converter 56 and stored in the microcontroller's buffer for processing. This allows the microcontroller 36 to calculate a running average of the measurements, for example, over the last forty readings, thus eliminating oscillation that may be introduced by the A/D converter.

The controller 30 has input means 40 to allow set-up parameters to be entered. Input means 40 may simply be a number of potentiometers which may be turned until the desired value reads out on the display 32, or may be a keypad or keyboard for entry of numeric or alphanumeric commands. In the experimental prototype, four input switches were used. These switches, numbered 1-4 controlled the following functions: 1) select primary menu; 2) select secondary menu; 3) change displayed numerical value up (or down); and 4) change displayed numerical value down (or up). Values to be input ahead of time include the zero, or starting value, for measurement, which may be necessary if the patient actually has one leg shorter than the other. (This input is entered in response to the prompt "MARK LEGS EVEN".) Other variables could be the distance between the stirrup and the longitudinal bar and the desired range and sensitivity for the LED bar graph display, if this option is available.

Provisions may be made for storing or printing out the data gathered before, during and after adjustment. If a separate computational and memory device is provided and interfaced to the controller 30, e.g., a personal computer, patient information may be entered before measurement begins so that the appropriate data will be entered on a chart which can then be printed out and placed in the patient's file, or saved on a disk.

Although the above description has specifically been directed toward a device and method for practicing the activator technique, the device is also adaptable to other types of tests which use joint displacement as a means for measuring a response. One such test is neuromuscular response which can be used in psychological evaluations to measure a patient's emotional response to certain stimuli where response causes muscle contraction and, thus, joint displacement. For such a test, the same device can be used or an apparatus similar to the one described above can be adapted for use on the patient's arms, with the stirrups being substituted by a pair of wrist cuffs or gloves, and the arms being supported on a measurement surface. Similarly, joint displacement can be used to conduct diagnostic testing in applied kinesiology, sacro-occipital technique, Brodie major/- minor system, acupuncture point testing, nutritional testing, emotional engram testing and allergy testing, among others. These measurements can be accomplished by measuring relative joint displacement in either the arms or the legs, or can be done by measuring time-varying displacement in a single limb.

It will be evident that there are additional embodiments and applications which are not disclosed in the detailed description but which clearly fall within the scope and spirit of the present invention. The specification is, therefore, not intended to be limiting, and the scope of the invention is to be limited only by the following claims.

We claim:

1. An apparatus for measuring relative leg length in a subject lying on a treatment table to facilitate chiropractic adjustment using an activator technique, where relative leg length is indicative of a difference between a left leg length and a right leg length of the subject, the apparatus comprising:
    a longitudinal bar disposed generally parallel to the subject's legs, said longitudinal bar having a first end and a second end;
    a transverse bar pivotally attached to said longitudinal bar, said transverse bar having a foot retaining means for retaining at least a portion of said subject's feet;
    pivoting attachment means for attaching said transverse bar to said longitudinal bar;
    a mounting means for attaching a first end of said longitudinal bar to said treatment table;
    a first detector means for providing a first electrical signal representative of a displacement of said transverse bar from said first end of said longitudinal bar;
    a second detector means for providing a second electrical signal representative of an angular deviation of said transverse bar from perpendicular to said longitudinal bar;
    a computational means for converting said first electrical signal and said second electrical signal into an output signal indicating relative leg length; and a display means for displaying a value of said relative leg length.

2. An apparatus as in claim 1 further comprising a third detector means for providing a third electrical signal representative of an angle at which said subject's knees are bent.

3. An apparatus as in claim 2 wherein said relative leg length is measured when said third electrical signal indicates 0 degrees when said subject's knees are not bent.

4. An apparatus as in claim 2 where said relative leg length is measured when said subject's knees are bent and said third electrical signal indicates a knee-bend angle between 0 degrees and 120 degrees, said knee-bend angle being an angle formed by raising said subject's feet above said treatment table.

5. An apparatus as in claim 1 wherein said output signal is calculated according to the relationship $L \pm d \sin \theta$ where L is leg length, $\theta$ is said angular deviation and d is one-half the distance between said subject's feet.

6. An apparatus as in claim 1 wherein said display means comprises an LCD display for providing at least one numerical value.

7. An apparatus as in claim 1 wherein said display means comprises an LED display for providing a bar graph indication of offset of relative leg length.

8. An apparatus as in claim 1 wherein said display means comprises a video monitor.

9. An apparatus as in claim 1 further comprising an audible indicator for providing an audible bar graph display of offset of relative leg length.

10. An apparatus as in claim 1 wherein said treatment table comprises a fixed segment and two slidable segments wherein said two slidable segments slide on rails parallel to the sides of said treatment table with each of said subject's legs being placed on a separate one of said two slidable segments.

11. An apparatus as in claim 1 further comprising a recessed area disposed in said treatment table wherein said mounting means is attached.

12. An apparatus for measuring joint displacement in a joint of a subject's limb caused by muscle tension, the apparatus comprising:
    a longitudinal bar having a first end and a second end, said longitudinal bar being disposed generally parallel to a direction of joint displacement;
    a transverse bar pivotally attached to said longitudinal bar, said transverse bar a retaining means for releasably attaching at least one of the subject's limbs which will be affected by joint displacement;
    pivoting attachment means for attaching said transverse bar to said longitudinal bar;
    a mounting means for attaching said first end of said longitudinal bar to a table;
    a first detection element for providing a first electrical signal representative of a displacement of said transverse bar from said first end of said longitudinal bar;
    a second detection element for providing a second electrical signal representative of an angular deviation of said transverse bar from perpendicular to said longitudinal bar;
    a computational means for converting said first electrical signal and said second electrical signal into an output signal indicating joint displacement; and
    a display means for displaying said output signal in the form of a value of said joint displacement.

13. An apparatus as in claim 12 wherein said output signal is calculated according to $L \pm d \sin \theta$ where L is limb length, $\theta$ is said angular deviation and d is a distance between said subject's limbs.

14. An apparatus as in claim 12 wherein said display means comprises an LCD display for providing at least one numerical value.

15. An apparatus as in claim 12 wherein said display means comprises an LED display for providing a bar graph indication of offset of joint displacement.

16. An apparatus as in claim 12 wherein said display means comprises a video monitor.

17. An apparatus as in claim 12 wherein said measurement table comprises a fixed segment and two slidable segments wherein said two slidable segments slide on rails parallel to the sides of said measurement table.

18. An apparatus as in claim 12 further comprising an audible indicator for providing an audible bar graph indication of offset of joint displacement.

19. A method for measuring relative leg length in a subject to facilitate chiropractic adjustment using an activator technique where said subject is lying on a supporting surface where relative leg length is indicative of a difference between a left leg length and a right leg length of the subject, the method comprising:

attaching a first end of a longitudinal bar on said supporting surface generally parallel to the subject's legs;

retaining a lower portion of the subject's legs in a retaining means on a transverse bar rotatably attached to said longitudinal bar;

detecting a displacement of said transverse bar from said first end of said longitudinal bar and generating a first electrical signal representative thereof;

detecting an angular deviation of said transverse bar from perpendicular to said longitudinal bar and generating a second electrical signal representative thereof;

converting said first electrical signal and said second electrical signal into an output signal indicating relative leg length; and displaying a value of said relative leg length.

20. A method as in claim 19 further comprising detecting a knee bend angle and generating a third electrical signal representative thereof.

21. A method as in claim 19 wherein the step of disposing a longitudinal bar on said supporting surface comprises recessing said longitudinal bar within said supporting surface.

22. A method for measuring relative joint displacement in a joint of a subject's limb caused by muscle tension, the method comprising:

attaching a first end of a longitudinal bar to a supporting surface generally parallel to a direction of joint displacement;

retaining at least a portion of said subject's limb which will be affected by the joint displacement in a retaining means on a transverse bar rotatably attached to said longitudinal bar;

detecting a deviation of said transverse bar from first said end of said longitudinal bar and generating a first electrical signal representative thereof;

detecting an angular deviation of said transverse bar from perpendicular to said longitudinal bar and generating a second electrical signal representative thereof;

converting said first electrical signal and said second electrical signal into an output signal indicating joint displacement length; and displaying a value of said joint displacement.

23. A method as in claim 22 wherein the step of disposing a longitudinal bar on said measurement surface comprises recessing said longitudinal bar within said measurement surface.

* * * * *